(12) United States Patent
Wu et al.

(10) Patent No.: US 12,127,685 B2
(45) Date of Patent: Oct. 29, 2024

(54) AUXILIARY TOOL FOR SURGERY

(71) Applicant: SCENERAY CO., LTD., Jiangsu (CN)

(72) Inventors: Guoliang Wu, Jiangsu (CN); Haitao Zhang, Jiangsu (CN)

(73) Assignee: SCENERAY CO., LTD., Jiangsu (CN)

( * ) Notice: Subject to any disclaimer, the term of this patent is extended or adjusted under 35 U.S.C. 154(b) by 260 days.

(21) Appl. No.: 17/771,933

(22) PCT Filed: Nov. 28, 2019

(86) PCT No.: PCT/CN2019/121535
§ 371 (c)(1),
(2) Date: Apr. 26, 2022

(87) PCT Pub. No.: WO2021/102780
PCT Pub. Date: Jun. 3, 2021

(65) Prior Publication Data
US 2022/0386778 A1    Dec. 8, 2022

(51) Int. Cl.
*A47C 4/14*    (2006.01)
*A47C 4/08*    (2006.01)

(52) U.S. Cl.
CPC . *A47C 4/14* (2013.01); *A47C 4/08* (2013.01)

(58) Field of Classification Search
CPC .................................................. A61N 1/0539
USPC ........................................ 606/129; 607/116
See application file for complete search history.

(56) References Cited

U.S. PATENT DOCUMENTS

| | | | |
|---|---|---|---|
| 7,580,756 B2* | 8/2009 | Schulte | A61N 1/0539 607/116 |
| 7,766,922 B1* | 8/2010 | Daglow | A61B 90/10 606/129 |
| 7,899,549 B2* | 3/2011 | Sweeney | A61N 1/056 600/424 |
| 8,425,534 B2* | 4/2013 | Barker | A61F 2/2875 607/45 |
| 8,731,686 B2* | 5/2014 | Lane | A61N 1/0539 607/116 |
| 8,845,656 B2* | 9/2014 | Skakoon | A61N 1/0534 606/129 |
| 9,572,973 B2* | 2/2017 | Chavez | A61F 2/2875 |

(Continued)

FOREIGN PATENT DOCUMENTS

| | | |
|---|---|---|
| CN | 102526873 A | 7/2012 |
| CN | 103550859 A | 2/2014 |

(Continued)

OTHER PUBLICATIONS

Extended European Search Report in Application No. 19954465.1 dated May 12, 2023, 7 pages.

(Continued)

*Primary Examiner* — Jose V Chen
(74) *Attorney, Agent, or Firm* — ArentFox Schiff LLP; Joseph M. Maraia

(57) ABSTRACT

An auxiliary tool for surgery includes an auxiliary tool main body part, and a first leg pair located on the auxiliary tool main body part. A tail end of the first leg pair is connected to the auxiliary tool main body part, a first mounting part is formed at a front end of the first leg pair, and the first mounting part is configured to clamp and press a surgical device to place the surgical device in a predetermined position.

17 Claims, 2 Drawing Sheets

(56) References Cited

U.S. PATENT DOCUMENTS

| | | | |
|---|---|---|---|
| 11,103,716 B2* | 8/2021 | Funderburk | A61N 1/3758 |
| 2004/0034367 A1 | 2/2004 | Malinowski | |
| 2009/0182351 A1* | 7/2009 | Malinowski | A61B 90/11 |
| | | | 606/142 |
| 2014/0257325 A1 | 9/2014 | Chavez et al. | |
| 2016/0375238 A1* | 12/2016 | Leven | A61N 1/0553 |
| | | | 607/116 |
| 2019/0275317 A1 | 9/2019 | Malinowski | |
| 2023/0083368 A1* | 3/2023 | Manicka | A61N 1/37512 |
| | | | 607/9 |
| 2023/0119177 A1* | 4/2023 | Smith | A61N 1/0539 |
| | | | 607/116 |

FOREIGN PATENT DOCUMENTS

| | | | |
|---|---|---|---|
| CN | 108325069 A | | 7/2018 |
| CN | 110215604 A | | 9/2019 |
| DE | 102015117326 A1 | | 4/2017 |
| JP | 2016202468 A | | 12/2016 |

OTHER PUBLICATIONS

International Search Report for related Application No. PCT/CN2019/121535 mailed Aug. 19, 2020.

* cited by examiner

AUXILIARY TOOL FOR SURGERY

CROSS-REFERENCE TO RELATED APPLICATION(S)

This is a national stage application filed under 37 U.S.C. 371 based on International Patent Application No. PCT/CN2019/121535, filed Nov. 28, 2019, disclosure of which is incorporated herein by reference in its entirety.

TECHNICAL FIELD

The present disclosure relates to the field of surgery, in particular, to an auxiliary tool for surgery.

BACKGROUND

In a surgery, such as an implantable surgery, during the patient's operation, firstly, the doctor needs to determine a target position of the patient's brain by a three-dimensional stereotactic device. According to the target position, the doctor opens a small hole on the patient's skull, and inserts a brain electrode cable into the target of the brain through the cranial hole. The doctor tests the implanted target with a test stimulator. If the stimulation treatment effect is ideal, the brain electrode cable is reliably fixed on the skull with a fixing device.

In the existing art, for example, in the U.S. Pat. No. 4,328,813, the fixing device for fixing the brain electrode cable usually includes a cranial ring and a cranial cover, after the brain electrode cable is inserted into the cranial ring, the cranial cover covers the cranial ring and closes the cranial ring. The brain electrode cable is clamped between the cranial cover and the cranial ring, and the brain electrode cable is fixed on the skull by the friction between the brain electrode cable and the cranial ring as well as the cranial cover.

However, during the operation, when the trocar is inserted and after the trocar is removed, since the brain electrode cable is not fixed, after taking out the guide wire in the cable, the doctor presses the cable on the cranial ring with the cranial cover directly. In this case, the cable is easily to be deviated and changed in a depth position, which makes the insertion position of the electrode deviate from the target and makes the operation complicated, resulting in unsatisfactory treatment effect. Moreover, since a layer of the cranial cover is added to the scalp of the patient, the height of the whole fixing device is too high, which is easy to cause discomfort and unsightly appearance of the patient.

Therefore, it is urgent to develop an auxiliary tool for surgical assistance to achieve the auxiliary fixing, especially the brain electrode fixing. The tool includes a cranial plug, which enables the electrode cable to be reliably fixed on the cranial ring in a horizontal plane, is convenient for accurately and reliably inserting the cranial plug into the hole of the cranial ring, facilitates the doctor use under different conditions, and improves the convenience of the doctor's operation.

SUMMARY

The purpose of the present disclosure is to provide an auxiliary tool for surgery, which assists the doctor in reliably fixing a cranial plug in a cranial ring during the operation process, so as to achieve the convenient insertion and the effective compression.

To achieve the purpose of the present disclosure, the present disclosure provides an auxiliary tool for surgery, including: an auxiliary tool main body part, and a first leg pair located on the auxiliary tool main body part. A tail end of the first leg pair is connected to the auxiliary tool main body part, a first mounting part is formed at a front end of the first leg pair, and the mounting part is configured to clamp and press a surgical device to place the surgical device in a predetermined position.

As a further improvement of the present disclosure, the first mounting part includes a first boss and at least one first protruding point disposed on the first boss.

As a further improvement of the present disclosure, the auxiliary tool further includes a second leg pair located on the auxiliary tool main body part. A tail end of the second leg pair is connected to the auxiliary tool main body part, and a front end of the second leg pair extends outward so as to form a second mounting part.

As a further improvement of the present disclosure, the second mounting part includes a second boss and a third boss structure disposed on the second boss, or the second mounting part includes a second boss and at least one second protruding point.

As a further improvement of the present disclosure, the surgical device has at least one hole matched with the at least one first protruding point of the mounting part.

As a further improvement of the present disclosure, a deformation space is provided between the first leg pair.

As a further improvement of the present disclosure, a length of the first leg pair is larger than a length of the second leg pair.

As a further improvement of the present disclosure, the first leg pair or the second leg pair further includes a friction structure.

As a further improvement of the present disclosure, the friction structure is a structure having multiple convex ribs or multiple point-shaped protruding structures.

As a further improvement of the present disclosure, the manufacturing material of the auxiliary tool for surgery with the above structure is engineering plastic or elastic metal material.

The auxiliary tool for surgery in the present disclosure assists the doctor in reliably fixing the cranial plug in the cranial ring during the operation process, which achieves the effective placement, fixation and compression, so that the electrode cable is firmly and accurately positioned at a designated target position, and the phenomenon of target deviation in the operation process of sealing the cranial ring is avoided, the operation process is reduced, and the whole surgery is convenient for operation.

DETAILED DESCRIPTION

Figure 1:
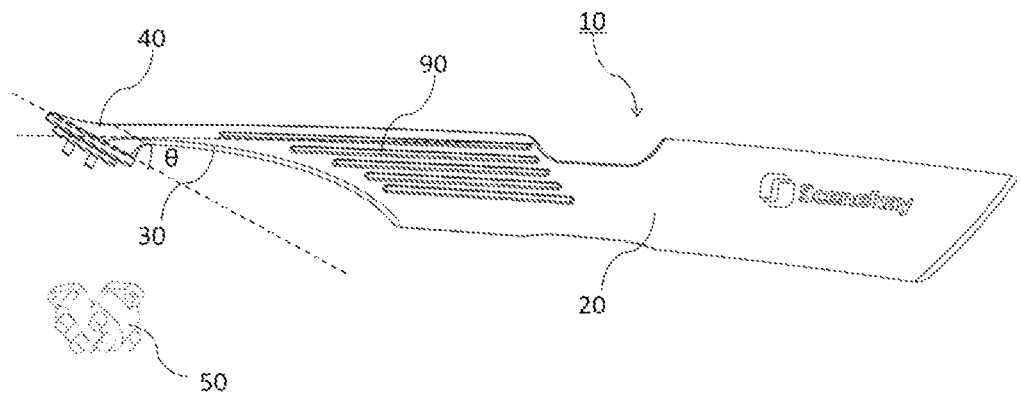
FIG. 1 is a structure diagram of the present disclosure.

The present disclosure will be described below in detail with reference to the specific embodiments illustrated in the accompanying drawings. However, these embodiments are not intended to limit the present disclosure. Any changes in structures, methods or functions made by those skilled in the art based on these embodiments are within the scope of the present disclosure.

Referring to FIGS. 1 to 4, an auxiliary tool for surgery 10 includes an auxiliary tool main body part 20, and a first leg pair 30 located on the auxiliary tool main body part. A tail end of the first leg pair 30 is connected to the auxiliary tool main body part 20, a first mounting part 40 is formed at a front end of the first leg pair 30, and the first mounting part 40 cooperates with an upper surface of a cranial foramen plug 50 for inserting the cranial foramen plug 50 into a hole of a cranial ring (not shown in the figure).

The first mounting part 40 includes a first boss 401 and at least one protruding point 402 disposed on the first boss 401. The boss 401 is cylindrical, and the diameter of the boss 401 is approximately same as the diameter of the cranial foramen plug 50. In this embodiment, four protruding points 402 are uniformly distributed on a circular bottom surface of the boss 401, and are configured to match with four grooves on an upper surface of the cranial foramen plug 50 so as to facilitate the doctor accessing to the cranial foramen plug 50. Apparently, in other embodiments, the cranial foramen plug 50 may be matched in other ways, such as changing the shape and the number of protruding points 402, as in the embodiment shown in FIG. 4, the number of protruding points 402 is two.

Figure 2:
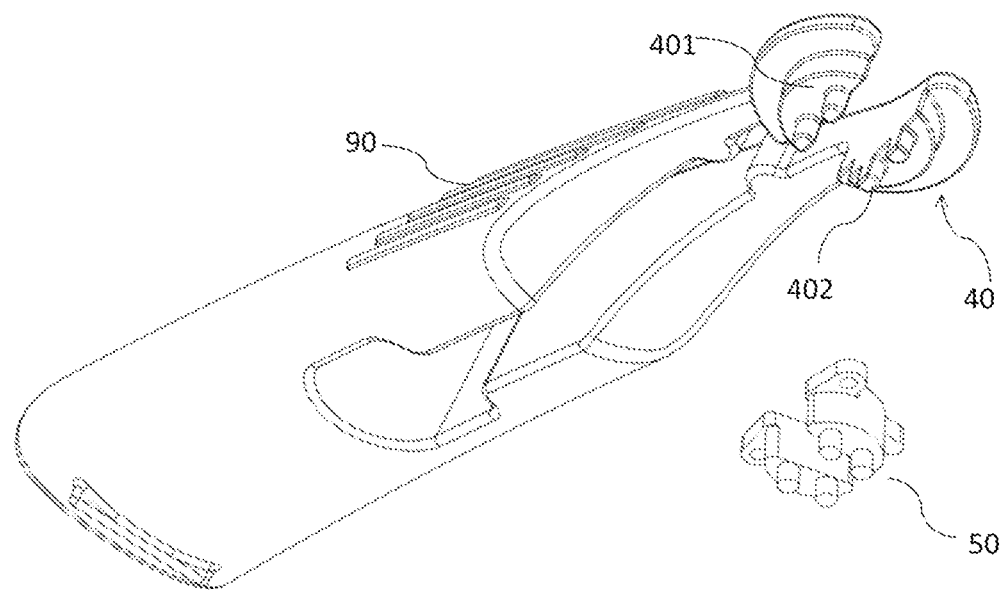
FIG. 2 is a schematic diagram from another perspective of the present disclosure.
Figure 3:
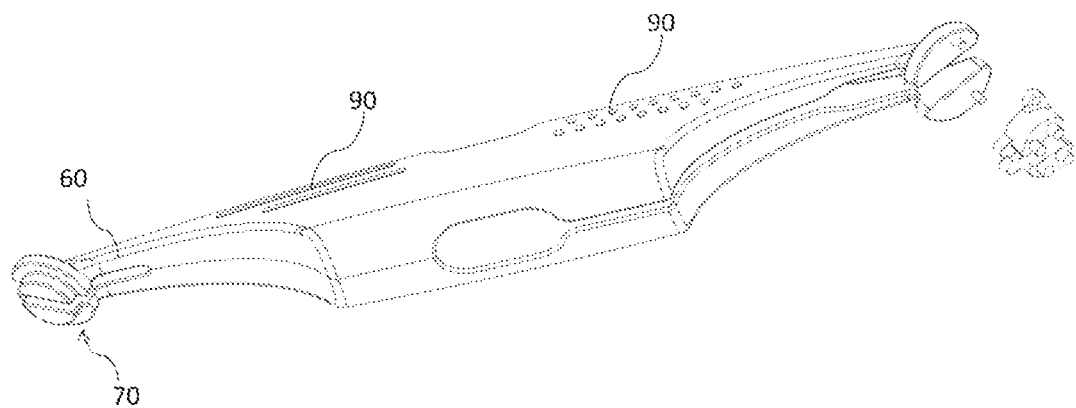
FIG. 3 is a structure diagram of another embodiment of the present disclosure.
Figure 4:
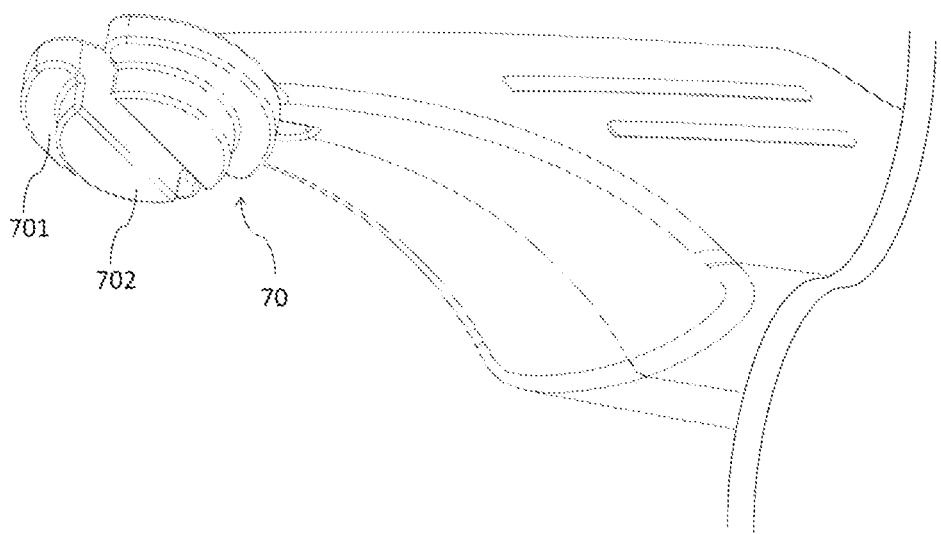
FIG. 4 is a schematic diagram of a second leg pair of an auxiliary tool for surgery according to the present disclosure.

As shown in FIGS. 1 and 2, a plane where the first boss 401 of the first mounting part 40 has an inclination angle θ with respect to an extension plane where the auxiliary tool main body part 20 is located, and a range of the inclination angle θ may be set to be $0°≤θ≤90°$. The inclination angle θ is set to facilitate applying a force to the first mounting part 40 when holding the auxiliary tool main body part 20. Preferably, the range of the inclination angle θ may be set to $10°≤θ≤60°$, and a more preferable range of the inclination angle θ is $15°≤θ≤45°$, $20°≤θ≤35°$. The inclination angle θ in the embodiment as shown in the figure is 30°. According to different force-applying habits of users, the inclination angle θ may also preferably be $30°≤θ≤60°$, $30°≤θ≤45°$ or the like.

The auxiliary tool 10 also includes a second leg pair 60 located on the auxiliary tool main body part 20, a tail end of the second leg pair 60 is connected to the auxiliary tool main body part 20, and a front end of the second leg pair 60 extends outward so as to form a second mounting part 70. The second mounting part 70 includes a second boss 701, and a third boss 702 disposed on the second boss 701. The diameter of the third boss 702 is slightly smaller than the diameter of the cranial foramen plug 50. The length of the first leg pair 30 is larger than the length of the second leg pair 60 of the auxiliary tool for surgery.

As described above, a plane where the second boss 701 of the second mounting part 70 is located and an extension plane where the auxiliary tool main body part 20 is located also have an inclination angle, and the inclination angle may be set with reference to the inclination angle θ between the plane where the first boss 401 is located and the extension plane where the auxiliary tool main body part 20 is located, which will not be described here.

The first leg pair and/or the second leg pair further include a friction structure 90. The friction structure 90 is a structure having multiple convex ribs or multiple point-shaped protruding structures.

The manufacturing material of the auxiliary tool for surgery in the present disclosure is engineering plastic or elastic metal material.

The use of the auxiliary tool for surgery during the operation process of the doctor will be described below in detail, especially the process of installing a cranial foramen electrode lock and an electrode by using the auxiliary tool for surgery.

First, the doctor first inserts the cranial ring into a cranial opening of the patient, and after the cooperation is firm, the doctor inserts the trocar in place. In this case, the trocar is fixed with a special clamp, and then a nerve stimulation electrode cable is inserted into a pre-calculated depth from an inner hole of the trocar. After the doctor completes the adjustment test, firstly, the doctor pinches two legs of the first leg pair of the auxiliary tool for surgery to insert four (exemplarily shown as four) protruding points 302 on the boss 301 into four corresponding grooves on the upper surface of the cranial plug 50, so that the cranial plug 50 is connected to the first mounting part 40. Since the auxiliary tool for surgery in the present disclosure is made of the engineering plastic or the elastic metal material, the doctor controls the opening of a side groove on the cranial plug 50 through the pinching force applied to the two leg of the first leg pair by the hand, and then clamps the trocar containing the electrode cable in an aligned position inside the cranial plug 50 and the auxiliary tool for surgery 10, and clamps the auxiliary tool for surgery by the hand and presses the auxiliary tool for surgery down forcefully so that the cranial plug 50 and the cranial ring are cooperated in place, and the cranial ring is closed by the cranial plug 40. The doctor may then further clamp one end of the auxiliary tool for surgery with the third boss 702 by the hand and press down the one end with the third boss 702 forcefully so that the cranial plug 50 fully cooperates with the cranial ring.

Next, the doctor continues to clamp one end of the auxiliary tool for surgery with the third boss 702 by the hand and press down the one end with the third boss 702 forcefully so that the cranial plug 40 and the cranial ring 50 keeps cooperating with each other in place, and then takes out the trocar in an axial direction of the trocar, avoiding the plane deviation or the axial deviation caused by the friction between the trocar and the cranial foramen plug 50. When the trocar is removed from the cranial foramen plug 50, the brain electrode lead cable can effectively maintain at this position since the brain electrode lead cable is tightly fixed by the cranial foramen plug 50 having elasticity.

Compared with the existing art, the doctor can quickly and conveniently insert and reliably fix the cranial foramen plug in the cranial ring by using this dedicate fixation auxiliary device in a relatively limited space. In addition, after the trocar is taken away and the guide wire in the cable is taken out, a stimulation cable is also clamped tightly by the cranial plug to prevent the cable from being displaced in horizontal and vertical directions, which is convenient for operation.

It is to be understood that although this specification is described in terms of the embodiments, not every embodiment includes only one independent solution. Such description mode of the specification is merely for the sake of clarity, and those skilled in the art should regard the specification as a whole. The technical solutions in the embodiments may also be appropriately combined to form other embodiments which will be understood by those skilled in the art.

A series of detailed descriptions set forth above are merely illustrative of the feasible embodiments of the present disclosure and are not intended to limit the scope of the present invention. Equivalent embodiments or alterations made without departing from the spirit of the present disclosure are within the scope of the present disclosure.

The invention claimed is:

1. An auxiliary tool for surgery, comprising:

an auxiliary tool main body part, a first leg pair, and a second leg pair, wherein the first leg pair and the second leg pair are located on the auxiliary tool main body part, wherein a tail end of the first leg pair is connected to one end of the auxiliary tool main body part, a first mounting part is formed at a front end of the first leg pair, and the first mounting part is configured to clamp and press a surgical device to place the surgical device in a predetermined position; and wherein a tail end of the second leg pair is connected to another end of the auxiliary tool main body part which is opposite to the one end of the auxiliary tool main body part, and a front end of the second leg pair extends outward so as to form a second mounting part.

2. The auxiliary tool for surgery of claim 1, wherein the first mounting part comprises a first boss, and at least one protruding point disposed on the first boss.

3. The auxiliary tool for surgery of claim 1, wherein the second mounting part comprises a second boss, and a third boss disposed on the second boss.

4. The auxiliary tool for surgery of claim 3, wherein a manufacturing material of the auxiliary tool for surgery is engineering plastic or elastic metal material.

5. The auxiliary tool for surgery of claim 2, wherein the surgical device has at least one groove matched with the at least one protruding point of the first mounting part.

6. The auxiliary tool for surgery of claim 5, wherein a manufacturing material of the auxiliary tool for surgery is engineering plastic or elastic metal material.

7. The auxiliary tool for surgery of claim 2, wherein a plane where the first boss is located has an inclination angle $\theta$ with respect to an extension plane where the auxiliary tool main body part is located, and a range of the inclination angle $\theta$ is set to be $0°\leq\theta\leq90°$.

8. The auxiliary tool for surgery of claim 7, wherein a manufacturing material of the auxiliary tool for surgery is engineering plastic or elastic metal material.

9. The auxiliary tool for surgery of claim 1, wherein a deformation space is provided between the first leg pair.

10. The auxiliary tool for surgery of claim 9, wherein a manufacturing material of the auxiliary tool for surgery is engineering plastic or elastic metal material.

11. The auxiliary tool for surgery of claim 1, wherein a length of the first leg pair is larger than a length of the second leg pair.

12. The auxiliary tool for surgery of claim 11, wherein a manufacturing material of the auxiliary tool for surgery is engineering plastic or elastic metal material.

13. The auxiliary tool for surgery of claim 1, wherein at least one of the first leg pair or the second leg pair further comprises a friction structure.

14. The auxiliary tool for surgery of claim 13, wherein the friction structure is a structure having a plurality of convex ribs or a plurality of point-shaped protruding structures.

15. The auxiliary tool for surgery of claim 13, wherein a manufacturing material of the auxiliary tool for surgery is engineering plastic or elastic metal material.

16. The auxiliary tool for surgery of claim 1, wherein a manufacturing material of the auxiliary tool for surgery is engineering plastic or elastic metal material.

17. The auxiliary tool for surgery of claim 2, wherein a manufacturing material of the auxiliary tool for surgery is engineering plastic or elastic metal material.

* * * * *